(12) United States Patent
Squires et al.

(10) Patent No.: US 10,105,234 B2
(45) Date of Patent: Oct. 23, 2018

(54) SPINAL IMPLANT SYSTEM AND METHODS OF USE

(71) Applicant: Warsaw Orthopedic, Inc., Warsaw, IN (US)

(72) Inventors: Craig M. Squires, Cordova, TN (US); Mark C. Dace, Collierville, TN (US); Nikhil Kulkarni, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 19 days.

(21) Appl. No.: 14/209,458

(22) Filed: Mar. 13, 2014

(65) Prior Publication Data

US 2015/0257795 A1 Sep. 17, 2015

(51) Int. Cl.
| | | |
|---|---|---|
| *A61B 17/70* | (2006.01) | |
| *A61F 2/44* | (2006.01) | |
| *A61B 17/80* | (2006.01) | |
| *A61F 2/46* | (2006.01) | |
| *A61B 17/00* | (2006.01) | |
| *A61F 2/30* | (2006.01) | |
| *A61F 2/28* | (2006.01) | |

(52) U.S. Cl.
CPC ........ *A61F 2/4455* (2013.01); *A61B 17/7059* (2013.01); *A61B 17/7071* (2013.01); *A61B 17/808* (2013.01); *A61B 17/8085* (2013.01); *A61F 2/4405* (2013.01); *A61F 2/4611* (2013.01); *A61B 2017/00933* (2013.01); *A61F 2/30767* (2013.01); *A61F 2002/2817* (2013.01); *A61F 2002/2835* (2013.01); *A61F 2002/3008* (2013.01); *A61F 2002/30013* (2013.01); *A61F 2002/30062* (2013.01); *A61F 2002/30092* (2013.01); *A61F 2002/30565* (2013.01); *A61F 2002/30571* (2013.01); *A61F 2002/30578* (2013.01); *A61F 2002/30677* (2013.01); *A61F 2310/00017* (2013.01); *A61F 2310/00023* (2013.01); *A61F 2310/00029* (2013.01); *A61F 2310/0097* (2013.01); *A61F 2310/00293* (2013.01); *A61F 2310/00359* (2013.01); *A61F 2310/00365* (2013.01); *A61F 2310/00976* (2013.01)

(58) Field of Classification Search
CPC ....................... A61B 17/7062–17/7071; A61B 17/80–17/8095; A61B 2017/7073
See application file for complete search history.

(56) References Cited

U.S. PATENT DOCUMENTS

| | | | | |
|---|---|---|---|---|
| 6,572,617 B1 * | 6/2003 | Senegas | ......................... | 606/263 |
| 8,926,664 B1 * | 1/2015 | Millhouse | .......... | A61B 17/7071 |
| | | | | 606/246 |
| 2003/0125738 A1 * | 7/2003 | Khanna | ......................... | 606/61 |

(Continued)

*Primary Examiner* — Jan Christopher Merene
*Assistant Examiner* — Steven Cotroneo (57) ABSTRACT

The spinal implant includes a tissue barrier. A first member extends in a transverse orientation from the tissue barrier and is connectable with vertebral tissue adjacent a lamina. A second member is spaced from the first member and extends in a transverse orientation from the tissue barrier. The second member is connectable with vertebral tissue adjacent a lamina. At least one of the members includes an end that is disposable about at least a portion of the vertebral tissue. Systems and methods of use are disclosed.

20 Claims, 7 Drawing Sheets

(56) References Cited

U.S. PATENT DOCUMENTS

| | | | |
|---|---|---|---|
| 2004/0030388 A1* | 2/2004 | Null | A61B 17/7059 623/17.11 |
| 2005/0043740 A1* | 2/2005 | Haid et al. | 606/90 |
| 2005/0273100 A1* | 12/2005 | Taylor | A61B 17/7035 623/17.11 |
| 2007/0225806 A1* | 9/2007 | Squires et al. | 623/17.11 |
| 2009/0318968 A1* | 12/2009 | Duggal | A61B 17/7026 606/250 |
| 2011/0106083 A1* | 5/2011 | Voellmicke et al. | 606/70 |
| 2011/0106169 A1* | 5/2011 | Zalenski | A61B 17/7071 606/279 |
| 2011/0125269 A1* | 5/2011 | Moskowitz et al. | 623/17.11 |
| 2011/0270397 A1* | 11/2011 | Mac-Thiong | 623/17.11 |
| 2012/0071931 A1* | 3/2012 | Perez-Cruet | A61B 17/7071 606/279 |
| 2012/0165942 A1* | 6/2012 | Khanna | 623/17.16 |
| 2013/0211524 A1* | 8/2013 | Hugues | 623/17.11 |
| 2014/0088648 A1* | 3/2014 | Chind | 606/251 |
| 2014/0114361 A1* | 4/2014 | Robinson | 606/281 |

\* cited by examiner

SPINAL IMPLANT SYSTEM AND METHODS OF USE

TECHNICAL FIELD

The present disclosure generally relates to spinal implants for the treatment of musculoskeletal disorders, and more particularly to a spinal implant system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, laminoplasty and implantable prosthetics. For example, laminoplasty treatments may employ implants, which may include plates and bone fasteners to stabilize vertebrae and facilitate healing. This disclosure describes an improvement over these prior art technologies.

SUMMARY

In one embodiment, a spinal implant is provided. The spinal implant includes a tissue barrier. A first member extends in a transverse orientation from the tissue barrier and is connectable with vertebral tissue adjacent a lamina. A second member is spaced from the first member and extends in a transverse orientation from the tissue barrier. The second member is connectable with vertebral tissue adjacent a lamina. At least one of the members includes an end that is disposable about at least a portion of the vertebral tissue. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the spinal implant system and related methods of use disclosed are discussed in terms of medical devices for the treatment of musculoskeletal disorders and more particularly, in terms of a spinal implant system that includes a spinal implant and a method for treating a spine. In one embodiment, the systems and methods of the present disclosure are employed with a laminoplasty procedure.

In one embodiment, the present disclosure provides a spinal implant system employed with a laminoplasty surgical technique that includes removing a portion of vertebral tissue, such as, for example, a portion of a spinous process and/or lamina and placing an implant adjacent and/or between the tissue adjacent a vertebra to form a bridge. In one embodiment, the spinal implant includes a plate. See also, the examples and disclosure of systems, spinal implants and methods shown and described in U.S. patent application Ser. No. 14/209,388 filed Mar. 13, 2014, and published as U.S. Patent Application Publication No. 20150257789, on Sep. 17, 2015, the entire contents of which being incorporated herein by reference.

In one embodiment, the present disclosure provides a spinal implant system employed with a french-door style cervical laminoplasty plate. In one embodiment, the spinal implant system includes an instrument. In one embodiment, the spinal implant system includes an implant having a curved section adjacent an intermediate portion thereof and configured to be contoured with a patient's natural anatomy, such as, for example, a spinal canal. In one embodiment, the spinal implant system includes a spinal implant having a roughened surface configured to mate with bone to provide stability during insertion. In one embodiment, the spinal implant includes additional surface area for bony integration. In one embodiment, the spinal implant is provided that includes a screw hole configured to receive a screw for attachment to bone.

In one embodiment, the spinal implant system includes a spinal implant including a dovetail opening configured for aligning with and attaching to a delivery instrument. In one embodiment, the spinal implant includes plate material configured for manipulation such that the spinal implant can be fit to a patients anatomy. In some embodiments, the spinal implant includes a material, such as, for example, a titanium sheet that is thin enough so it can be bent to match a shape of a spinous process and/or a lamina. In one embodiment, the spinal implant system includes an insertion instrument that includes a dovetail portion configured for mating with a dovetail opening of a spinal implant. In one embodiment, the insertion instrument includes an opening configured for disposal of a surgical instrument, such as, for example, a drill, tap, and/or a screw driver.

In one embodiment, a spinal implant is provided that maintains space between vertebral tissue where tissue is removed and is configured to receive a graft or scaffold. In one embodiment, the spinal implant includes a portion for receiving the graft or scaffold to facilitate bone growth. In one embodiment, the scaffold is integrated with the spinal implant. In one embodiment, the scaffold is independent from the spinal implant and is attached to the spinal implant in situ or prior to implantation. In one embodiment, the scaffold is configured to bridge the two sides of a lamina together.

In one embodiment, the spinal implant includes a scaffold configured for disposal with a notch in vertebral tissue, such as for example, a lamina, transverse process, pars interarticularis, facet or spinous process. In one embodiment, the spinal implant includes a surface adjacent the spinal cord. In one embodiment, the surface adjacent to the spinal cord is smooth to prevent irritation to the spinal cord. In one embodiment, the surface adjacent to the spinal cord is configured as a tissue barrier to prevent a fusion mass from growing into the spinal canal.

In some embodiments, the present disclosure may be employed to treat spinal disorders such as, for example, degenerative disc disease, disc herniation, osteoporosis, spondylolisthesis, stenosis, tumor and fractures. In some embodiments, the present disclosure may be employed with other osteal and bone related applications, including those associated with diagnostics and therapeutics. In some embodiments, the disclosed spinal implant system and methods may be alternatively employed in a surgical treatment with a patient in a prone or supine position, and/or employ various surgical approaches to the spine, including posterior, posterior mid-line, medial, lateral, postero-lateral approaches, and in other body regions. The spinal implant system and methods of the present disclosure may also be alternatively employed with procedures for treating the lumbar, cervical, thoracic and pelvic regions of a spinal column. The spinal implant system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
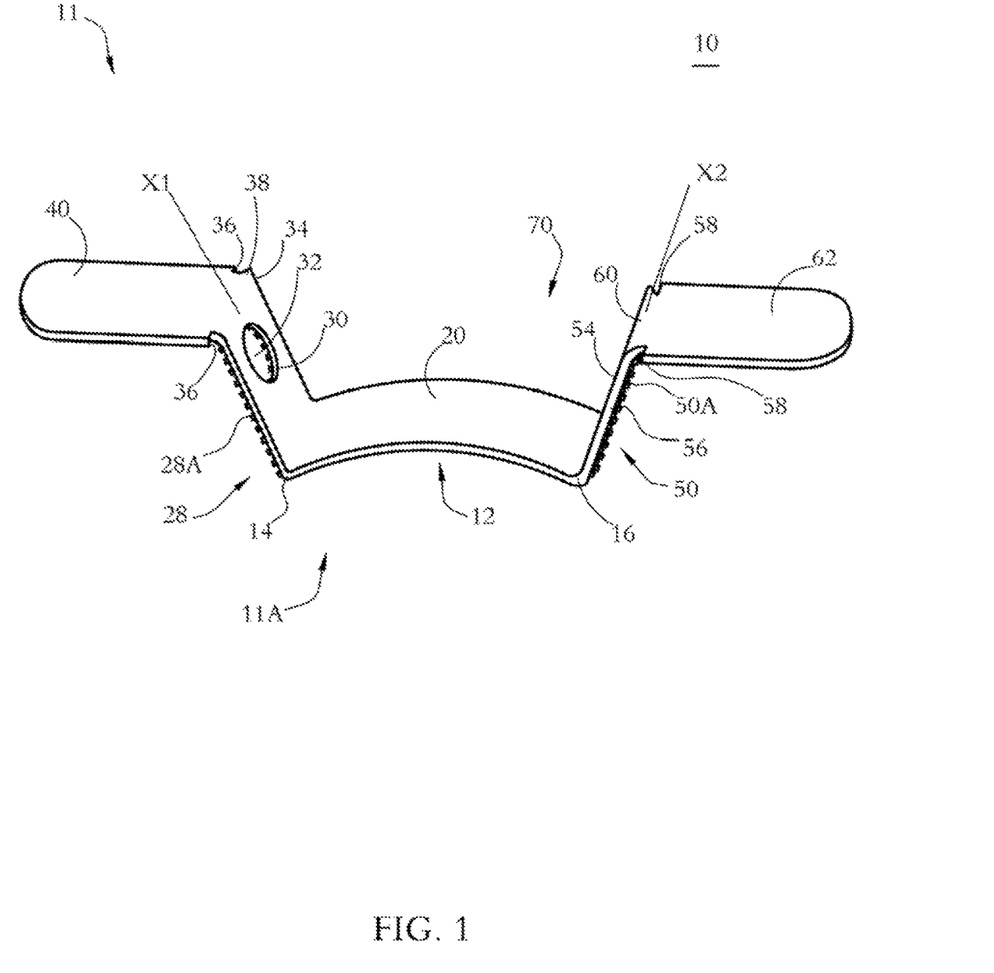
FIG. 1 is a perspective view of a component of one embodiment of a system in accordance with the principles of the present disclosure.

The following discussion includes a description of a spinal implant system and related methods of employing the spinal implant system in accordance with the principles of the present disclosure. Alternate embodiments are also disclosed. Reference is made in detail to the exemplary embodiments of the present disclosure, some of which are illustrated in the accompanying figures. Turning to FIG. 1, there are illustrated components of a spinal implant system 10 including a spinal implant in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$^4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials.

Spinal implant system 10 can be employed, for example, in laminoplasty procedures to treat patients suffering from a spinal disorder to provide stabilization and decompression. The components of spinal implant system 10 may be monolithically formed, integrally connected or include fastening elements and/or instruments, for example, as described herein.

Spinal implant system 10 includes a spinal implant 11 configured for disposal with vertebral tissue in a laminoplasty procedure to treat patients suffering from a spinal disorder to provide stabilization and decompression. In some embodiments, spinal implant 11 is configured for stabilizing vertebral tissue, such as, for example, divided and/or separated lamina, transverse process, pars interarticularis, facet or spinous process portions of one or more vertebral levels, as shown and described for example with regard to FIGS. 5 and 6. In some embodiments, spinal implant 11 is configured for stabilizing one or more vertebral levels via attachment with a vertebral level having removed, non-separated portions of vertebral tissue, such as, for example, a lamina, transverse process, pars interarticularis, facet or spinous process, for example, such that a cavity, relief or notch is created in the vertebral tissue, however, the tissue is not separated and spaced apart, as shown and described for example with regard to FIG. 8.

Spinal implant 11 includes a plate 11a having a tissue barrier 12. Tissue barrier 12 extends longitudinally between an end 14 and an end 16, and includes a portion 20 disposed intermediate and/or therebetween. Tissue barrier 12 includes a wall having a substantially uniform, rectangular cross section. In some embodiments, tissue barrier 12 can have alternate configurations, such as, tubular, oval, oblong, irregular, undulating, non-uniform, variable, hollow, wire, mesh and/or tapered.

End 16 is spaced apart from end 14 and portion 20 has a non-planar face, such as, for example, an arcuate configuration including a curvature that is oriented adjacent tissue, such as, for example, a spinal canal. In some embodiments, portion 20 can face and/or engage adjacent, opposing, and/or distributed locations of vertebral tissue, as described herein, of a posterior, posterior mid-line, medial, lateral and/or postero-lateral portion of vertebrae. In some embodiments, portion 20 can comprise alternate configurations, such as, for example, concave, linear or angled.

End 14 includes a member, such as, for example, a transverse extension 28 that extends from portion 20 at an angular orientation. Extension 28 defines a longitudinal axis X1. Extension 28 includes a fixation surface, such as, for example, surface 28a oriented to face and/or engage vertebral tissue, such as, for example, a lamina. In one embodiment, all or only a portion of extension 28 is engageable with a cut surface of tissue, as described herein. In one embodiment, surface 28a is roughened to facilitate engagement with tissue and provides an initial provisional fixation with tissue. In some embodiments, surface 28a is smooth, porous, textured, rough, porous, semi-porous, dimpled and/or polished.

In some embodiments, extension 28 can comprise a member that abuts and/or engages a separated surface of an anterior facing portion of vertebral tissue, as described herein. In some embodiments, extension 28 can extend from portion 20 at various angular orientations, such as, for example, acute, obtuse and in a range of 0-360 degrees. In some embodiments, extension 28 can extend from portion 20 in a perpendicular, transverse, substantially aligned, twisted or helical orientation.

Figure 5:
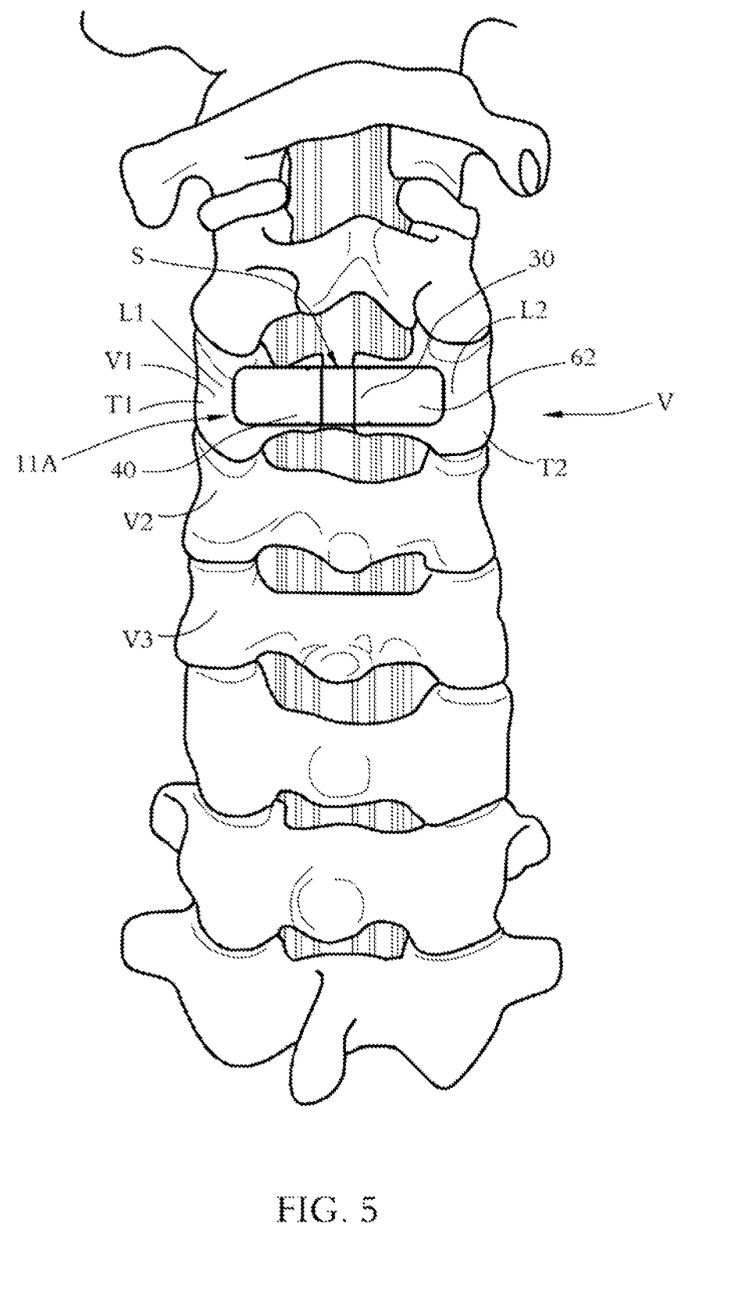
FIG. 5 is a plan view of components of one embodiment of a system in accordance with the principles of the present disclosure disposed with vertebrae.

Extension 28 includes an inner surface 30 that defines a cavity, such as, for example, an aperture 32 configured to receive a bone fastener, such as, for example, a bone screw 26, as discussed herein and shown in FIG. 5. Bone screw 26 attaches extension 28 and spinal implant 11 with vertebral tissue, as described herein. In some embodiments, extension 28 may include one or a plurality of cavities configured for disposal of a bone fastener. In some embodiments, extension 28 may include an elongated slot for disposal of a bone fastener such that disposal of spinal implant 11 with vertebral tissue is selectively adjustable. In some embodiments, spinal implant system 10 includes one or more of fasteners that may be engaged with vertebral tissue in various orientations, such as, for example, series, parallel, offset, staggered and/or alternate vertebral levels. In some embodiments, the fasteners may comprise pedicle screws, monoaxial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Extension 28 includes an outer surface 34. A portion of surface 34 comprises a mating element having a dovetail configuration that defines apertures 36. In one embodiment, apertures 36 are dovetail in shape. Apertures 36 are configured for engagement with a mating element of a delivery instrument, as discussed herein. In one embodiment, apertures 36 are disposed along a top edge 38 of extension 28. In some embodiments, apertures 36 can be disposed at alternate locations along a periphery of extension 28.

Extension 28 includes an end, such as, for example, a flange 40 configured for plastic deformation to conform to vertebral tissue. In some embodiments, flange 40 is malleable and can be shaped to conform to vertebral tissue prior to implant or in situ. In some embodiments, flange 40 can extend from extension 28 at various angular orientations, such as, for example, acute, obtuse and in a range of 0-360 degrees. In some embodiments, flange 40 can extend from extension 28 in a perpendicular, transverse, substantially aligned, twisted or helical orientation.

End 16 includes a member, such as for example a transverse extension 50 that extends from portion 20 at an angular orientation. Extension 50 defines a longitudinal axis X2. Extension 50 includes a fixation surface, such as, for example, surface 50a oriented to face and/or engage vertebral tissue, such as, for example, a lamina. In one embodiment, all or only a portion of extension 50 is engageable with a cut surface of tissue, as described herein. In one embodiment, surface 50a is roughened to facilitate engagement with tissue and provides an initial provisional fixation with tissue. In some embodiments, surface 28a is smooth, porous, textured, rough, porous, semi-porous, dimpled and/or polished.

In some embodiments, extension 50 can comprise a member that abuts and/or engages a separated surface of an anterior facing portion of vertebral tissue, as described herein. In some embodiments, extension 50 can extend from portion 20 at various angular orientations, such as, for example, acute, obtuse and in a range of 0-360 degrees. In some embodiments, extension 50 can extend from portion 20 in a perpendicular, transverse, substantially aligned, twisted or helical orientation.

Extension 50 includes an inner surface 52 that defines a cavity, such as, for example, an aperture 54 configured to receive a bone fastener, such as, for example, bone screw 26, as discussed herein. Bone screw 26 attaches extension 50 and spinal implant 11 with vertebral tissue, as described herein. In some embodiments, extension 50 may include one or a plurality of cavities configured for disposal of a bone fastener. In some embodiments, extension 50 may include an elongated slot for disposal of a bone fastener such that disposal of spinal implant 11 with vertebral tissue is selectively adjustable.

Extension 50 includes an outer surface 56. A portion of surface 56 comprises a mating element having a dovetail configuration that defines apertures 58. In one embodiment, apertures 58 are dovetail in shape. Apertures 58 are configured for engagement with a mating element of a delivery instrument, as discussed herein. In one embodiment, apertures 58 are disposed along a top edge 60 of extension 50. In some embodiments, apertures 58 can be disposed at alternate locations along a periphery of extension 50.

Extension 50 includes an end, such as, for example, a flange 62 configured for plastic deformation to conform to vertebral tissue. In some embodiments, flange 62 is malleable and can be shaped to conform to vertebral tissue prior to implant or in situ. In some embodiments, flange 62 can extend from extension 50 at various angular orientations, such as, for example, acute, obtuse and in a range of 0-360 degrees. In some embodiments, flange 62 can extend from extension 50 in a perpendicular, transverse, substantially aligned, twisted or helical orientation.

In one embodiment, all or only a portion of plate 11 is fabricated from a work hardenable material such that deformation of flange 40 and/or flange 62 stiffens extensions 28, 50. In one embodiment, extensions 28, 50 are monolithically formed with plate 12. In one embodiment, extensions 28, 50 are separate and attachable with plate 12 in situ or prior to implantation. In one embodiment, flanges 40, 62 are monolithically formed with extensions 28, 50. In one embodiment, flanges 40, 62 are separate and attachable to extensions 28, 50 in situ or prior to implantation.

Portion 20 and extensions 28, 50 comprise a bone graft scaffold that defines a cavity 70. Cavity 70 is configured for disposal of bone growth promoting material. In some embodiments, the bone growth promoting material can include bone graft, allograft, xenograft, autograft, bone paste, bone chips, Skelite®, BMP and/or a titanium mesh material, such as, for example, Trabeculite™ available from Tecomet, Wilmington, Mass. In some embodiments, cavity 70 may include one or more agents, as described herein. In some embodiments, extensions 28, 50 may have a solid configuration. In one embodiment, extensions 28, 50 include an outer surface having perforations that communicate with bone growth promoting material disposed within cavity 70. In one embodiment, cavity 70 has a cage configuration.

In one embodiment, spinal implant 11 includes a bone graft scaffold configured to facilitate bone growth across at least a portion of spinal implant 11 and/or adjacent vertebral tissue connected with spinal implant, as described herein. The bone growth scaffold is connected with plate 11a in a configuration to grow bone and bridge vertebral tissue of one or more vertebral levels to treat patients suffering from a spinal disorder to provide stabilization and decompression.

Figure 2:
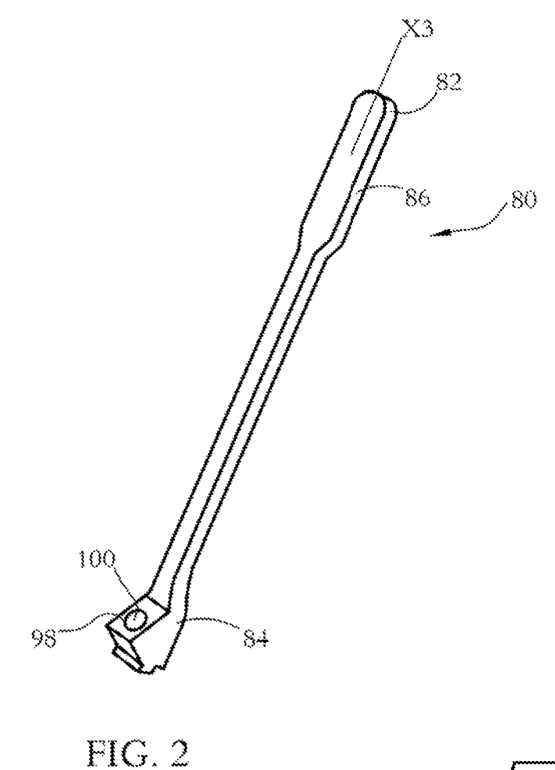
FIG. 2 is a perspective view of a component of one embodiment of a system in accordance with the principles of the present disclosure.
Figure 3:
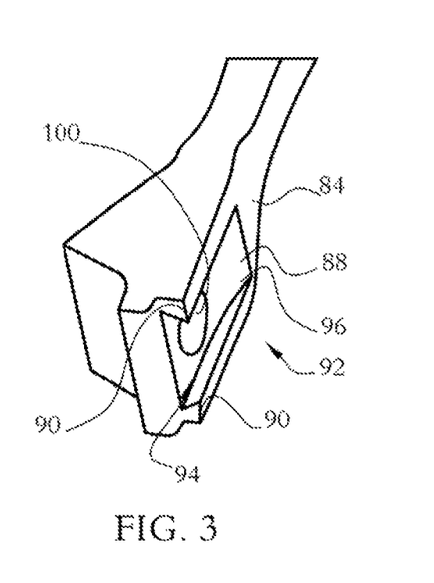
FIG. 3 is a break away, perspective view of the component shown in FIG. 2.
Figure 4:
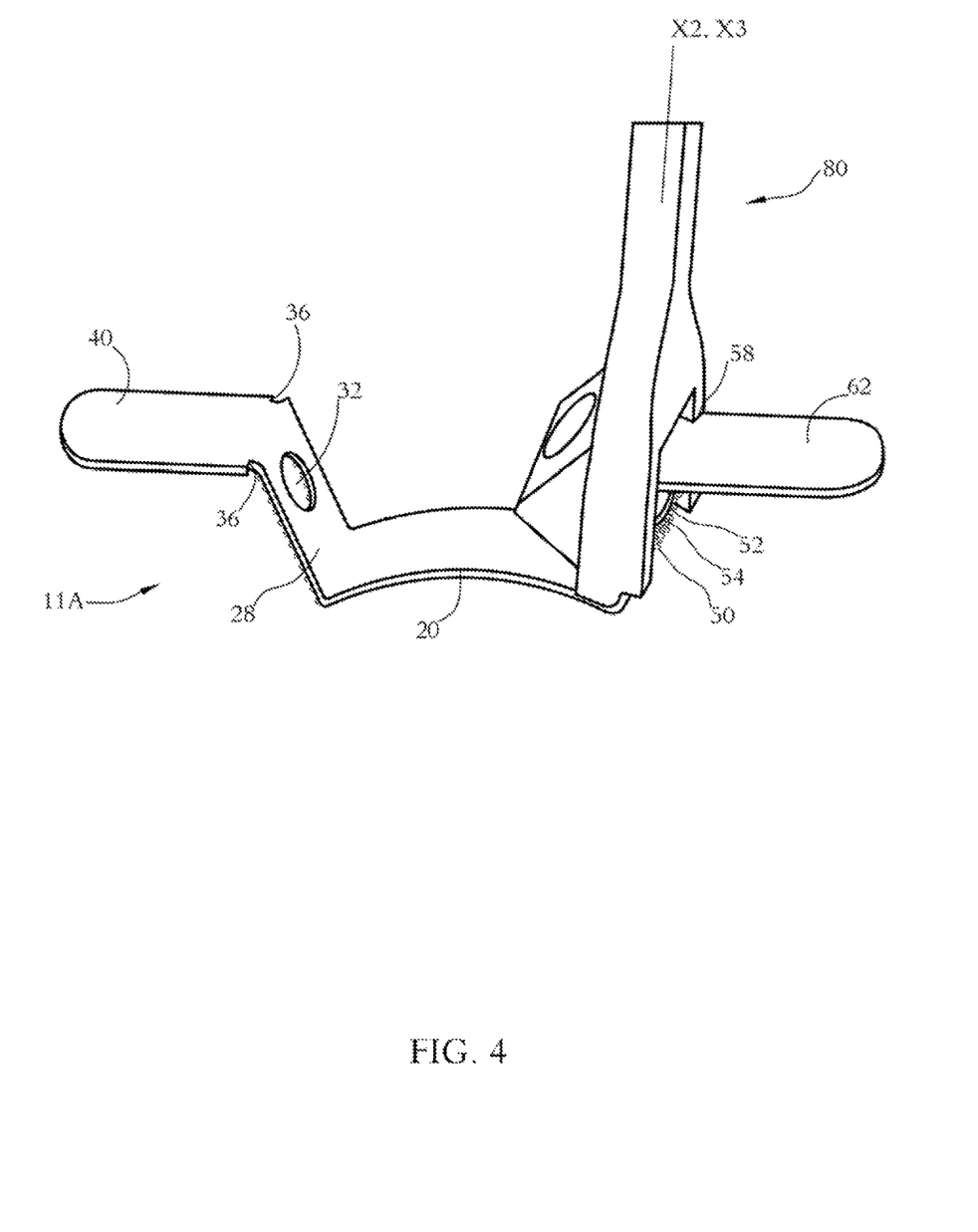
FIG. 4 is a perspective view of components of one embodiment of a system in accordance with the principles of the present disclosure.

In one embodiment, spinal implant system 10 includes a surgical instrument, such as, for example, a surgical delivery instrument 80, as shown in FIGS. 2-4, configured to facilitate manipulation, introduction, delivery and/or positioning of spinal implant 11. Instrument 80 extends between a proximal end 82 and a distal end 84 and defines a longitudinal axis X3. End 82 includes a handle 86 configured to facilitate manipulation of instrument 80. End 84 includes an outer surface 88 that defines a mating element, such as, for example, walls 90. Walls 90 define a cavity 92. In one embodiment, cavity 92 is configured for disposal of extension 50, as shown in FIG. 4, and/or extension 28 (not shown).

Walls 90 define channels 94 having a dovetail configuration and being disposed to receive extension 50 such that axis X2 is disposed in alignment with axis X3. Walls 90 are received within apertures 58. Extension 50 is configured to translate along channel 94 such that apertures 58 engage portion 96. In one embodiment, instrument 80 engages extension 28, similar to extension 50.

Instrument 80 includes a guide, such as, for example, an inner surface 98 that defines an opening 100. Opening 100 is configured for alignment with aperture 32 and/or aperture 54. Opening 100 is configured for disposal of a fastener, such as, for example, bone screw 26 and/or surgical instruments, such as, for example, a drill, tap, and/or a screw driver to facilitate engagement with bone screw 26, for guidance and/or alignment with aperture 32 and/or aperture 54 and/or tissue, as described herein.

Figure 6:
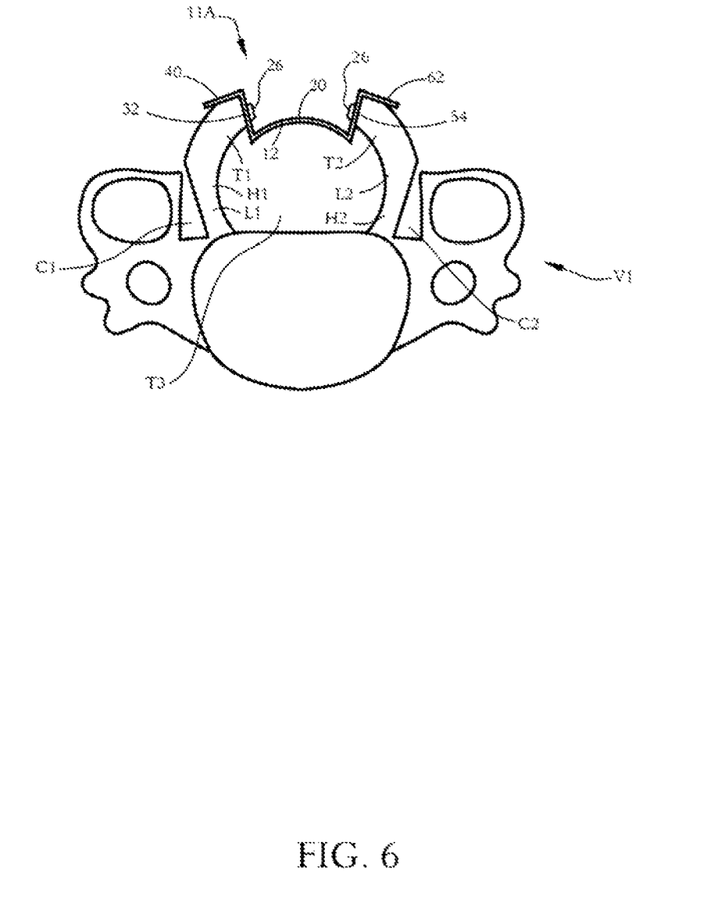
FIG. 6 is an axial view of components of one embodiment of a system in accordance with the principles of the present disclosure disposed with vertebrae.

In operation, use and assembly, as shown in FIGS. 4-6, spinal implant system 10, similar to the systems and methods described herein, is employed with a surgical procedure, such as, for example, a laminoplasty treatment of a spine of a patient including vertebrae V. Spinal implant system 10 may also be employed with other surgical procedures, such as, for example, discectomy, laminotomy, laminectomy, nerve root retraction, foramenotomy, facetectomy, decompression, and spinal, nucleus or disc replacement. For example, vertebral levels V1, V2 and V3 of vertebrae V can be removed, cut and/or weakened to open access and/or communication with a spinal canal T3 and/or spinal canal tissue, to provide space for a spinal cord. In one embodiment, spinal implant system 10 stabilizes vertebral levels V1, V2 and V3 for treatment and healing.

In use, to treat the affected section of vertebrae V, a medical practitioner obtains access to a surgical site including posterior elements of vertebrae V in any appropriate manner, such as through incision and retraction of tissues. In one embodiment, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Spinal implant 11 is employed to augment the surgical treatment. Spinal implant 11 can be delivered or implanted as a pre-assembled device or can be assembled in situ. Spinal implant 11 can be completely or partially revised, removed or replaced in situ. In one embodiment, one or all of the components of spinal implant system 10 can be delivered to the surgical site via manipulation and/or a free hand technique. An incision is made in the body of a patient and a cutting instrument (not shown) creates a surgical pathway for delivery of the components of spinal implant system 10 including spinal implant 11 within the patient body to adjacent vertebral level V1.

In one embodiment, as shown in FIG. 5, a cutting instrument (not shown) is employed to engage a spinous process (not shown-removed) of vertebral level V1. The spinous process is removed with the cutting instrument to form a cavity, gap or space S between lamina L1 and lamina L2. A relief C1 is cut down a medial cortical layer of lamina L1 to create a bone hinge H1, as shown in FIG. 6. A relief C2 is cut down the medial cortical layer of lamina L2 to create a bone hinge H2. In some embodiments, reliefs C1, C2 can include a groove, gutter or trough, and be formed using a high-speed burr drill. In one embodiment, reliefs C1, C2 have a depth of approximately 3 to 4 millimeters and a width of approximately 3 millimeters. In some embodiments, the associated ligamentum flavum, capsule, and/or veins adjacent vertebral level V1 can be separated to allow outward rotation of the separated laminae L1, L2.

Instrument 80 is engaged with implant 11 as shown in FIG. 4. As shown, channels 94 receive extension 50, as described herein, such that axes X2, X3 are aligned. Channel 94 translates along extension 50 such that extension 50 engages portion 96. Opening 100 is disposed in alignment with aperture 54. Instrument 80 is manipulated to deliver implant 11 adjacent the surgical site.

Flanges 40, 62 are positioned to face and/or engage a posterior surface of lamina L1 and lamina L2. In one embodiment, flanges 40, 62 are manipulated to deform, as described herein, about lamina L1 and lamina L2 of vertebral level V1 for engagement and/or fixation with the vertebral tissue of vertebral level V1 Lamina L1 is rotated outwardly about bone hinge H1 and lamina L2 is rotated outwardly about bone hinge H2 to enlarge the cross-sectional area of spinal canal T3. Plate 11a is positioned with space S between the separated surfaces of tissue T1, T2. Extensions 28, 50 are disposed with lamina L1 and lamina L2 to provide stabilization and decompression.

In some embodiments, extensions 28, 50 and plate 11a can prevent the separated laminae from closing from an implant position toward an original, non-implant position. In one embodiment, extensions 28, 50 tightly abut the spaced apart laminae.

Plate 11a is positioned in alignment for connection with vertebral level V1 for attachment of flange 40 with tissue T1 of lamina L1 and flange 62 with tissue T2 of lamina L2. Surfaces 28a, 50a are roughened and provide a provisional fixation of implant 11 to allow for alignment of screws 26. A pilot hole or the like is formed in tissue T1 and extension 28 is disposed such that aperture 32 is aligned with the pilot hole in tissue T1. Screw 26 is disposed with aperture 32 and inserted, drilled or otherwise fixed to tissue T1 to attach extension 28 with lamina L1. A pilot hole or the like is formed in tissue T2 and extension 50 is disposed such that aperture 54 is aligned with the pilot hole in tissue T2. Screw 26 is disposed with aperture 54 and inserted, drilled or otherwise fixed to tissue T2 to attach extension 50 with lamina L2. In some embodiments, instrument 80 comprises a guide for alignment of screws 26 and/or surgical instruments, as described herein, to orient and attach screws 26 with tissue for fixation of plate 11a with the laminae.

One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In one embodiment, spinal implant system 10 may include one or a plurality of spinal implants 11 for use with a single vertebral level or a plurality of vertebral levels.

In one embodiment, spinal implant system 10 includes an agent, which may be disposed, packed or layered within, on or about the components and/or surfaces of spinal implant 11. In one embodiment, the agent may include bone growth promoting material, such as, for example, bone graft to enhance fixation of the fixation elements with vertebrae. In one embodiment, the agent may include one or a plurality of therapeutic agents and/or pharmacological agents for release, including sustained release, to treat, for example, pain, inflammation and degeneration, Upon completion of the procedure, the non-implanted components, instruments and assemblies are removed and the incision(s) is closed.

Figure 7:
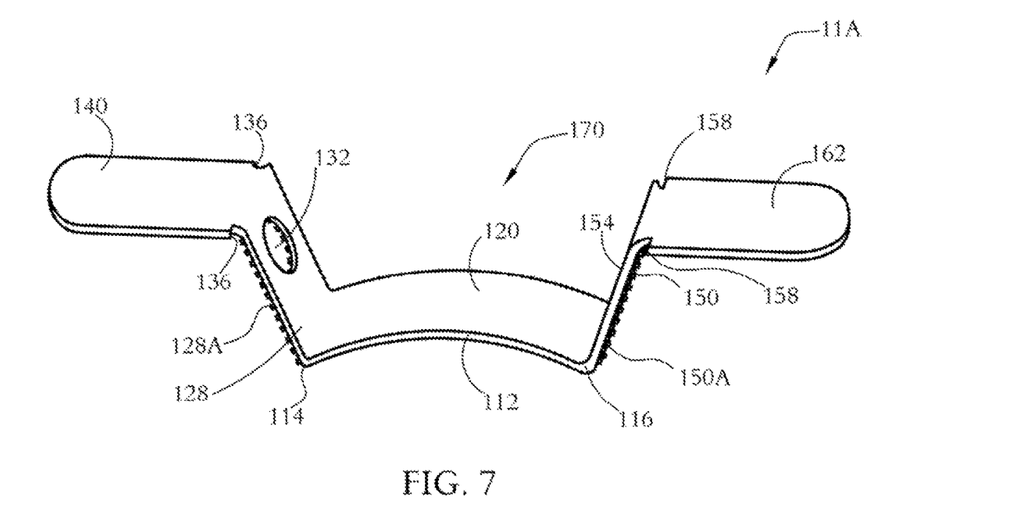
FIG. 7 is a perspective view of a component of one embodiment of a system in accordance with the principles of the present disclosure.
Figure 8:
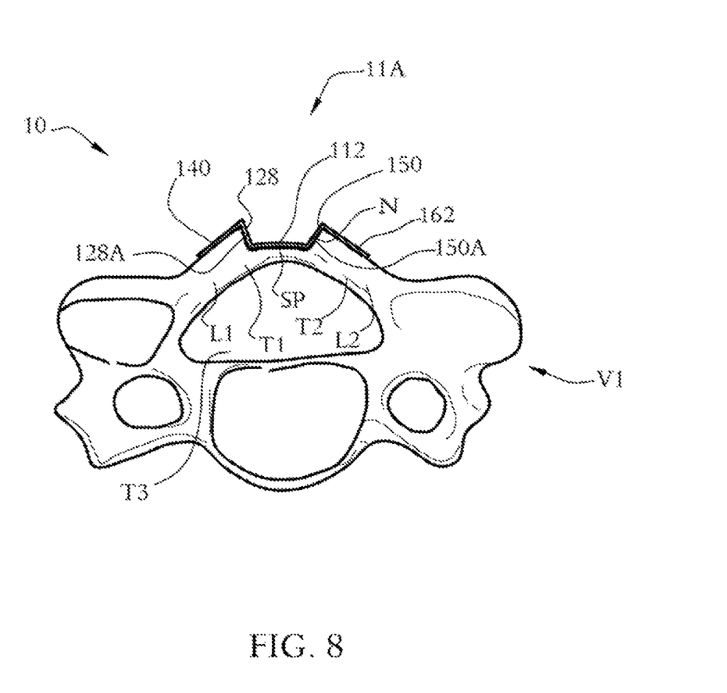
FIG. 8 is an axial view of components of one embodiment of a system in accordance with the principles of the present disclosure disposed with vertebrae.

In one embodiment, as shown in FIGS. 7 and 8, spinal implant system 10, similar to the systems and methods described above with regard to FIGS. 1-5, includes spinal implant 11, which is employed with a laminoplasty treatment such that plate 11a, as described herein, is configured for stabilizing one or more vertebral levels via attachment with vertebral level V1, which has removed, non-separated portions of vertebral tissue.

Plate 11a includes a tissue barrier 112, similar to tissue barrier 12 described herein, which extends longitudinally between an end 114 and an end 116, and includes a portion 120 disposed therebetween. Tissue barrier 112 is configured and dimensioned to fit within a notch formed in laminae.

End 114, similar to end 14 described herein, includes an extension 128 that extends from portion 120 at an angular orientation. Extension 128 includes surface 128a oriented to face and/or engage lamina. Extension 128 includes an aperture 132 configured to receive a bone screw, as discussed herein. Extension 128 includes apertures 136 configured to receive a delivery instrument, as described herein. Extension 128 includes flange 140 configured for plastic deformation to conform to vertebral tissue, as described herein.

End 116, similar to end 16 described herein, includes extension 150 that extends from portion 120 at an angular orientation. Extension 150 includes surface 150a oriented to face and/or engage lamina. Extension 150 includes an aperture 154 configured to receive a bone screw. Extension 150 includes apertures 158 configured to receive a delivery instrument. Extension 150 includes flange 162 configured for plastic deformation to conform to vertebral tissue. Portion 120 and extensions 128, 150 comprise a bone graft scaffold and form a cavity 170, similar to that described herein.

In use, to treat the affected section of vertebrae V, a high speed burring drill is employed to engage a spinous process SP of vertebral level V1 to form a notch N in the vertebral tissue. Spinous process SP is not separated and spaced apart. Plate 11a is disposed about lamina L1 and lamina L2, as described herein, for engagement and/or fixation with vertebral tissue T1, T2. Plate 11a having bone growth promoting material and/or an agent disposed therewith, as described herein, is positioned with notch N and/or extending external to notch N adjacent vertebral level V1 in a configuration to grow bone and bridge vertebral tissue to provide stabilization and decompression. Extensions 128, 150 are fastened with vertebral level V1, as described herein. Plate 11a is configured for disposal within notch N to prevent spinal implant 11 from irritating and/or undesirably engaging tissue of spinal canal T3, and/or preventing bone growth into spinal canal T3.

Figure 9:
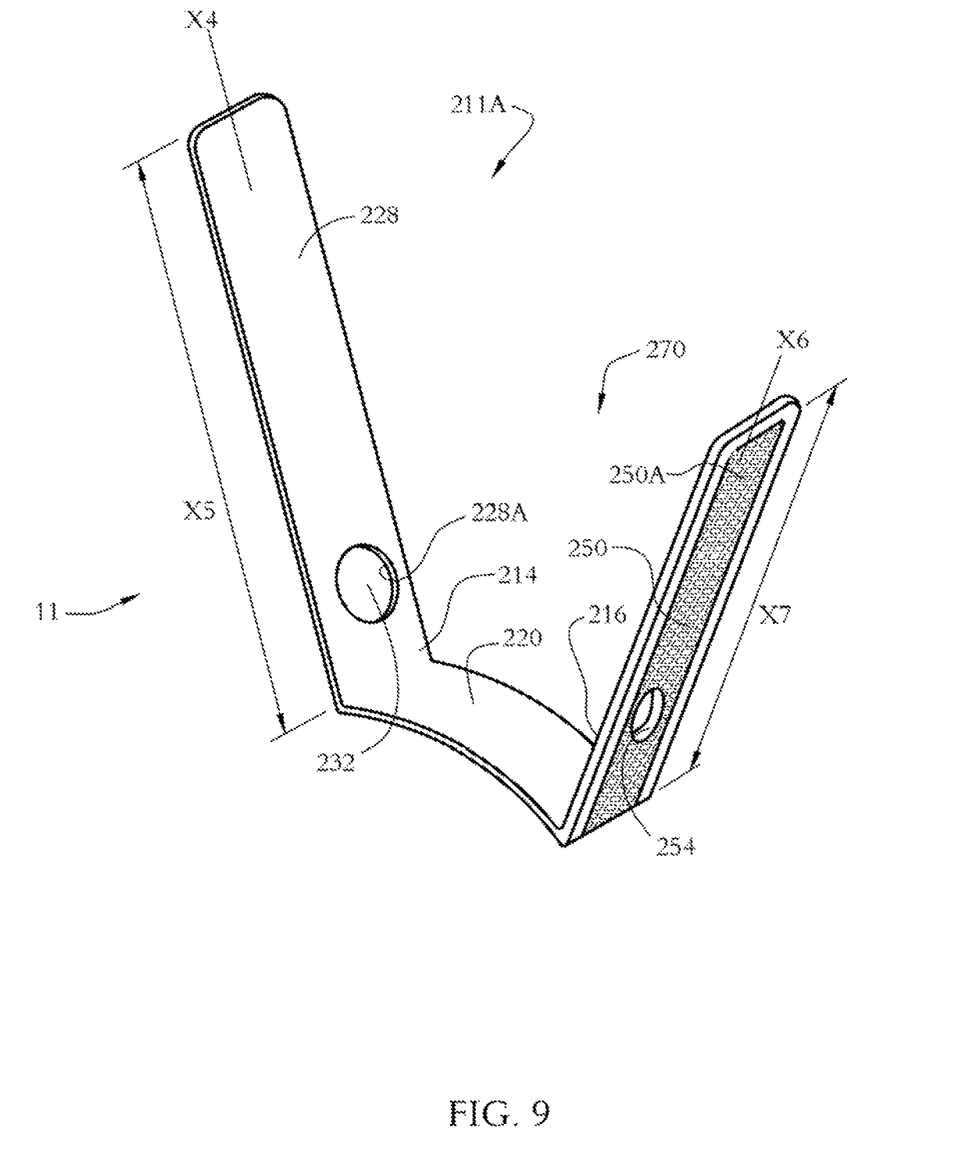
FIG. 9 is a perspective view of a component of one embodiment of a system in accordance with the principles of the present disclosure.

In one embodiment, as shown in FIG. 9, spinal implant system 10, similar to the systems and methods described herein, comprises spinal implant 11 having a plate 211a, similar to plate 11a described herein. Plate 211a includes an end 214 having an extension 228, similar to extension 28 described herein, and an end 216 having an extension 250, similar to extension 50 described herein.

Plate 211a includes a portion 220, similar to portion 20 described with regard to FIGS. 1-5, disposed between ends 214, 216. Extension 228 extends from portion 220 at an angular orientation. Extension 228 includes surface 228a, similar to surface 28a described with regard to FIGS. 1-5, and oriented to face and/or engage vertebral tissue. Extension 228 includes an aperture 232 configured to receive a bone screw, as discussed herein. Extension 228 extends along a longitudinal axis X4 and defines a length X5. Extension 228 is deformable, similar to that described herein, to conform to vertebral tissue prior to implant or in situ.

Extension 250 extends from portion 220 at an angular orientation. Extension 250 includes surface 250a, similar to surface 50a described with regard to FIGS. 1-5, and oriented to face and/or engage vertebral tissue. Extension 250 includes an aperture 254 configured to receive a bone screw. Extension 250 extends along a longitudinal axis X6 and defines a length X7. Extension 250 is deformable, similar to that described herein, to conform to vertebral tissue prior to implant or in situ. Portion 20 and extensions 228, 250 comprise a bone graft scaffold and form a cavity 270, similar to that described herein. In use, plate 211a is employed to treat an affected section of vertebrae V, similar to the methods described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a tissue barrier comprising a convex surface and a concave surface opposite the convex surface;
a first flat plate extending in a transverse orientation from the convex surface and connectable with vertebral tissue adjacent a lamina, the first plate comprising a first aperture that extends through a thickness of the first plate; and
a second flat plate spaced from the first plate and extending in a transverse orientation from the convex surface, the second plate being connectable with vertebral tissue adjacent a lamina, the second plate comprising a second aperture that extends through a thickness of the second plate and is aligned with the first aperture, the second aperture being spaced apart from the first aperture by the tissue barrier,
wherein the spinal implant includes a first flange extending from the first plate in a transverse orientation such that the first flange extends away from the second plate and a second flange extending from the second plate in a transverse orientation such that the second flange extends away from the first plate, the convex surface being positioned above the concave surface, the flanges each being positioned above the convex surface and disposable about at least a portion of the vertebral tissue.

2. A spinal implant as recited in claim 1, wherein the concave surface is configured to be oriented adjacent a spinal canal when the plates are connected to vertebral tissue adjacent a lamina.

3. A spinal implant as recited in claim 1, wherein the concave surface is oriented to face a spinal canal and is continuously curved from the first plate to the second plate.

4. A spinal implant as recited in claim 1, wherein each of the plates includes an outer roughened surface engageable with the vertebral tissue, the roughened surfaces facing away from one another.

5. A spinal implant as recited in claim 1, wherein the flanges are plastically deformable.

6. A spinal implant as recited in claim 1, wherein the plates are fabricated from a work hardenable material such that deformation of the flanges stiffen the plates.

7. A spinal implant as recited in claim 1, further comprising a bone graft scaffold disposed adjacent the tissue barrier and between the plates.

8. A spinal implant as recited in claim 1, wherein the convex surface and the concave surface each have a continuous radius of curvature from the first plate to the second plate.

9. A spinal implant as recited in claim 1, wherein each of the plates includes an outer roughened surface engageable with the vertebral tissue, the outer roughened surfaces each comprising a plurality of spaced apart projections that define recesses therebetween.

10. A spinal implant as recited in claim 1, wherein the spinal implant comprises a titanium sheet that is thin enough so that it can be bent to match a shape of a spinous process and/or lamina.

11. A spinal implant as recited in claim 1, wherein the flanges are both positioned in a transverse plane.

12. A spinal implant as recited in claim 1, wherein the first flange extends parallel to the second flange in a transverse plane.

13. A spinal implant as recited in claim 1, wherein the flanges are both free of any openings.

14. A spinal implant comprising:
a tissue barrier comprising a concave surface oriented to face a spinal canal and an opposite convex surface that define a wall thickness of the tissue barrier, the convex surface being positioned above the concave surface;
a flat plate defining a first transverse extension extending from the convex surface and fastenable with vertebral tissue adjacent a lamina, the first extension including a malleable end disposable about the vertebral tissue, the malleable end comprising a first aperture that extends through a thickness of the first extension; and
a flat plate defining a second transverse extension spaced from the first extension and extending from the convex surface, the second extension being fastenable with vertebral tissue adjacent a lamina and including a malleable end disposable about the vertebral tissue, the malleable ends each being positioned above the convex surface, the malleable end of the second extension comprising a second aperture that extends through a thickness of the second extension and is aligned with the first aperture, the second aperture being spaced apart from the first aperture by the tissue barrier, wherein the concave surface has a continuous radius of curvature from the first transverse extension to the second transverse extension.

15. A spinal implant as recited in claim 14, wherein the apertures are each configured to orient a fastener for penetrating a cut surface of the vertebral tissue.

16. A spinal implant system comprising:
a plate including a tissue barrier and spaced flat plates defining first and second transverse extensions that each extend in a transverse orientation from a convex surface of the tissue barrier, the tissue barrier comprising a concave surface opposite the convex surface, the convex surface being positioned above the concave surface, each extension having an opening disposed to orient a fastener for penetrating vertebral tissue adjacent laminae and an end disposable about at least a portion of the vertebral tissue, the openings each extending through a thickness of one of the extensions, the openings being aligned, the openings being spaced apart from one another by the tissue barrier, at least one of the extensions including a first mating element, the plate further including a first flange extending from the first member in a transverse orientation such that the first flange extends away from the second member and a second flange extending from the second member in a transverse orientation such that the second flange extends away from the first member, the flanges each being positioned above the convex surface; and
a surgical delivery instrument including a second mating element engageable with the first mating element.

17. A spinal implant system as recited in claim 16, wherein the second mating element includes a dovetail configuration engageable with the first mating element.

18. A spinal implant system as recited in claim 16, wherein:
the first mating element comprises a pair of apertures disposed along a top edge of the second transverse extension; and
the second mating element comprises a pair of walls each extending in a transverse orientation from an outer surface of the instrument such that the outer surface and inner surfaces of the walls define a cavity configured for disposal of the second transverse extension such that the walls are received within the apertures.

19. A spinal implant system as recited in claim 18, wherein the instrument comprises a hole extending through the outer surface and an opposite surface of the instrument such that the hole is positioned between the walls, the hole being aligned with the opening in the second transverse extension when the second mating element engages the first mating element.

20. A spinal implant system as recited in claim 16, wherein the instrument comprises a hole extending opposite surfaces of the instrument, the hole being aligned with the opening in the second transverse extension when the second mating element engages the first mating element such that the fastener can extend through the hole and the opening in the second transverse extension to penetrate the vertebral tissue.

* * * * *